United States Patent
Zeijlemaker et al.

(10) Patent No.: US 6,944,489 B2
(45) Date of Patent: Sep. 13, 2005

(54) METHOD AND APPARATUS FOR SHUNTING INDUCED CURRENTS IN AN ELECTRICAL LEAD

(75) Inventors: Volkert A. Zeijlemaker, Landgraaf (NL); Ron Kalin, New Hope, MN (US); Gregory A. Hrdlicka, Plymouth, MN (US); Yong Kyun Cho, Maple Grove, MN (US); James D. Reinke, Maple Grove, MN (US); Laurie D. Foerster, Mound, MN (US)

(73) Assignee: Medtronic, Inc., Minneapolis, MN (US)

( * ) Notice: Subject to any disclaimer, the term of this patent is extended or adjusted under 35 U.S.C. 154(b) by 547 days.

(21) Appl. No.: 10/059,512

(22) Filed: Jan. 29, 2002

(65) Prior Publication Data

US 2003/0083726 A1 May 1, 2003

Related U.S. Application Data

(63) Continuation-in-part of application No. 09/999,381, filed on Oct. 31, 2001.

(51) Int. Cl.[7] .................................................. A61B 5/04
(52) U.S. Cl. .................. 600/373; 600/374; 600/377; 607/116; 607/119; 607/122
(58) Field of Search .................... 607/115–116, 119, 607/122–123; 600/373–381

(56) References Cited

U.S. PATENT DOCUMENTS

| | | | |
|---|---|---|---|
| 4,320,763 A | 3/1982 | Money | 607/9 |
| 4,887,609 A | 12/1989 | Cole, Jr. | 128/696 |
| 5,217,010 A | 6/1993 | Tsitlik et al. | 607/9 |
| 5,325,870 A | 7/1994 | Kroll et al. | 607/122 |
| 5,366,496 A | 11/1994 | Dahl et al. | 607/132 |
| 5,629,622 A | 5/1997 | Scampini | 324/247 |
| 5,697,958 A | 12/1997 | Paul et al. | 607/31 |
| 5,722,998 A | 3/1998 | Prutchi et al. | 607/30 |
| 5,824,029 A | 10/1998 | Weijand et al. | 607/122 |
| 5,843,135 A * | 12/1998 | Weijand et al. | 607/17 |
| 6,070,101 A | 5/2000 | Struble et al. | 607/9 |
| 6,081,748 A | 6/2000 | Struble et al. | 607/9 |
| 6,101,417 A | 8/2000 | Vogel et al. | 607/30 |
| 6,122,545 A | 9/2000 | Struble et al. | 607/9 |
| 6,148,234 A | 11/2000 | Struble | 607/28 |
| 6,671,550 B2 * | 12/2003 | Iaizzo et al. | 607/27 |
| 2003/0013948 A1 * | 1/2003 | Russell | 600/372 |

FOREIGN PATENT DOCUMENTS

| | | | |
|---|---|---|---|
| WO | WO 00/48512 | 8/2000 | A61B/5/055 |
| WO | WO 02/083236 A2 * | 10/2002 | A61N/1/37 |

* cited by examiner

*Primary Examiner*—Carl Layno
(74) *Attorney, Agent, or Firm*—Girma Wolde-Michael

(57) ABSTRACT

An electrical lead includes an elongate body having a proximal end portion and a distal end portion, a first electrode disposed adjacent and joined to the distal end portion of the elongate body. Current flow within the first electrode is limited when a predetermined condition occurs, such as the generation of an electromagnetic field having a predetermined frequency range. The medical electrical lead may further comprise one or more second electrodes disposed adjacent the first electrode and joined to the elongate body to shunt current to body tissue when the predetermined condition occurs.

34 Claims, 5 Drawing Sheets

METHOD AND APPARATUS FOR SHUNTING INDUCED CURRENTS IN AN ELECTRICAL LEAD

RELATED APPLICATIONS

This application is a continuation-in-part of application Ser. No. 09/999,381 filed Oct. 31, 2001 entitled "Apparatus and Method for Shunting Induced Currents in an Electrical Lead".

FIELD OF THE INVENTION

This invention relates to a method and apparatus for providing electrical stimuli to tissue or receiving electrical stimuli corresponding to one or more conditions in tissue.

DESCRIPTION OF THE RELATED ART

Since the introduction of the first implantable pacemakers in the 1960s, there have been considerable advancements in both the fields of electronics and medicine, such that there is presently a wide assortment of commercially available body-implantable electronic medical devices. The class of implantable medical devices (IMDs) now includes therapeutic and diagnostic devices, such as pacemakers, cardioverters, defibrillators, neural stimulators, and drug administering devices, among others. Today's state-of-the-art implantable medical devices are vastly more sophisticated and complex than their early counterparts, and are capable of performing significantly more complex tasks. The therapeutic benefits of such devices have been well proven.

Modern electrical therapeutic and diagnostic devices for the heart require a reliable electrical connection between the device and a region of the heart. Typically, an electrical contact, commonly referred to as a "lead," is used for the desired electrical connection. One type of commonly used implantable lead is a transvenous lead. Transvenous leads are generally positioned through the venous system to attach and/or electrically connect at their distal end via a tip electrode to the heart. At their proximal end, they are typically connected to the electrical therapeutic and/or diagnostic device, which may be implanted. Such leads normally take the form of a long, flexible, insulated conductor. Among the many advantages of transvenous leads is that they permit an electrical contact with the heart without physically exposing the heart itself, i.e., major thoracic surgery is not required.

Other advancements in medical technology have led to improved imaging technologies, for example magnetic resonance imaging (MRI). MRI generates cross-sectional images of a human body by using nuclear magnetic resonance (NMR). The MRI process begins with positioning the body to be imaged in a strong, uniform magnetic field, which polarizes the nuclear magnetic moments of protons within hydrogen molecules in the body by forcing their spins into one of two possible orientations. Then an appropriately polarized radio-frequency field, applied at resonant frequency, forces spin transitions between these orientations. The spin transitions create a signal, an NMR phenomenon, which can be detected by a receiving coil.

Further, shortwave diathermy, microwave diathermy, ultrasound diathermy, and the like have been shown to provide therapeutic benefits to patients, such as to relieve pain, stiffness, and muscle spasms; to reduce joint contractures; to reduce swelling and pain after surgery; to promote wound healing; and the like. Generally, energy (e.g., shortwave energy, microwave energy, ultrasound energy, or the like) is directed into a localized area of the patient's body.

Traditionally, however, use of these technologies have been discouraged for patients having such implanted medical devices, as the environment produced by the MRI or diathermy apparatuses is generally considered hostile to such implantable medical devices. The energy fields, generated during the MRI or diathermy processes, may induce an electrical current in leads of implantable medical devices. In conventional leads, the electrical current is typically dissipated via the lead's tip electrode into tissue adjacent the distal end of the lead. The dissipation of this electrical current may cause resistive heating in the tissue adjacent the electrode and may result in damage to the tissue in some cases.

The present invention is directed to overcoming, or at least reducing, the effects of one or more of the problems set forth above.

SUMMARY OF THE INVENTION

In one aspect of the present invention, an electrical lead is presented. The medical electrical lead includes an elongate body having a proximal end portion and a distal end portion, a first electrode disposed adjacent and joined to the distal end portion of the elongate body, and a first conductor extending between the proximal end portion and the distal end portion of the elongate body and being electrically coupled to the first electrode. The medical electrical lead further comprises a second electrode disposed adjacent the first electrode and joined to the elongate body and a capacitive device electrically coupled to the first conductor and the second electrode. The lead further includes a current-limiting component within the lead body to limit the flow of current through the first electrode. Current may be limited upon detection of a predetermined condition, such as the existence of an electromagnetic field within a predetermined frequency range.

The current-limiting component may include an inductor, an active circuit component such as a Field Effect Transistor (FET), or a Micro-Electrical-Mechanical system (MEMs) switch. This component may be activated by a signal generated by a Hall-Effect sensor or another magnetic field sensor.

In another aspect of the present invention, a shunting assembly is presented. The shunting assembly includes an electrode, a conductor, and a capacitive device electrically coupled with the electrode and the conductor. The shunting assembly further comprises a device to limit current within the electrode upon detection of a predetermined condition, such as an electromagnetic field within a predetermined frequency range.

In another aspect of the present invention, a method is presented including selectively limiting current in a primary current path within a lead body when a predetermined condition is present. During this time, current may be directed via a secondary path to body tissue.

BRIEF DESCRIPTION OF THE DRAWINGS

The invention may be understood by reference to the following description taken in conjunction with the accompanying drawings, in which the leftmost significant digit(s) in the reference numerals denote(s) the first figure in which the respective reference numerals appear, and in which.

Figure 1:
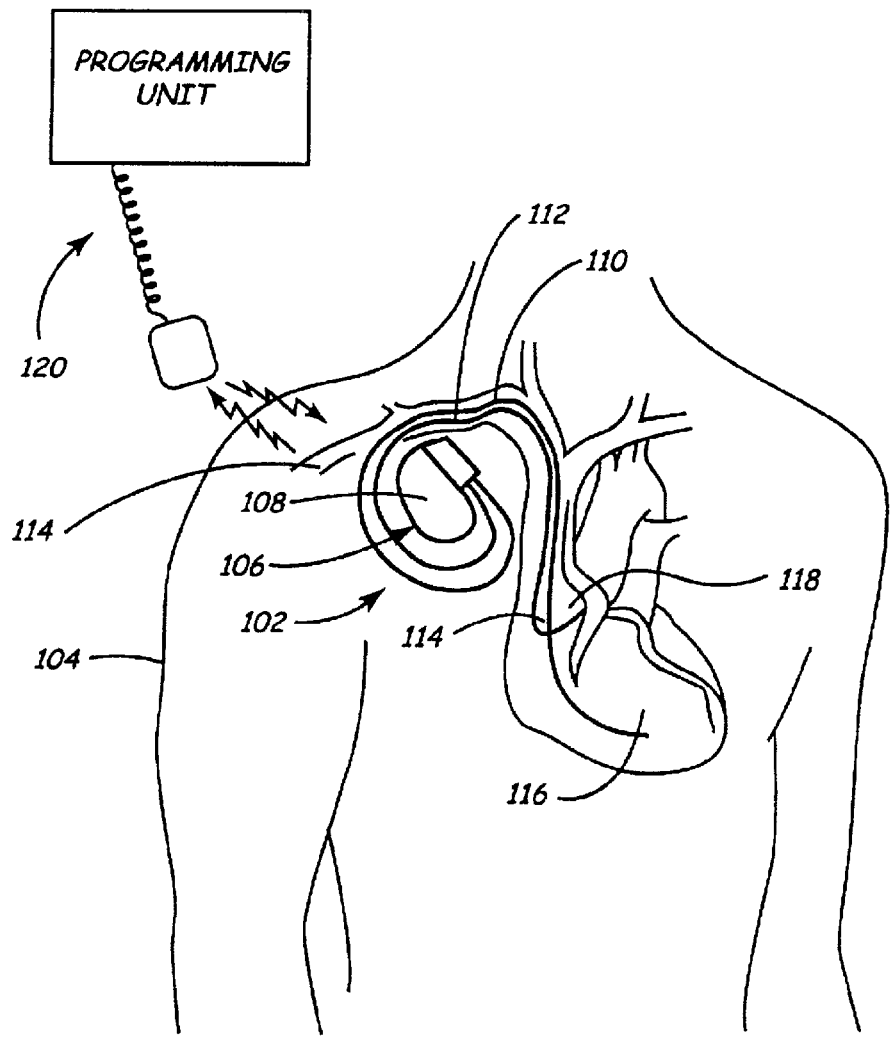
FIG. 1 is a stylized view of an embodiment of an implantable medical device according to one embodiment of the present invention, which has been implanted in a human body.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

Embodiments of the present invention concern body-implantable medical devices having one or more leads that may be used to stimulate a tissue of a body and/or sense one or more conditions in the tissue. Examples of such implantable medical devices are implantable coronary pacing devices, pulse generators, defibrillators, neural stimulation devices, electrogram devices, and the like. Generally, these devices operate by monitoring one or more conditions in the tissue and/or by delivering electrical stimuli to the tissue via the lead or leads. For example, such devices may be used to sense cardiac activity, to deliver electrical pacing stimuli to a portion or portions of a heart, to deliver electrical defibrillating stimuli to a portion or portions of the heart, to deliver electrical stimuli to a nerve, to deliver electrical stimuli to a portion or portions of a nerve bundle, or to deliver electrical stimuli to a portion or portions of a brain. While the description provided herein is directed to an implantable medical device used in a coronary setting, the present invention encompasses any implantable medical device, such as those described above, used in any setting.

FIG. 1 illustrates an embodiment of an implantable medical device 102 according to the present invention that has been implanted in a patient 104. The implantable medical device 102 includes an implantable electronic device 106 (e.g., a control unit or the like) housed within a hermetically-sealed, biologically-inert canister 108. The canister 108 may itself be conductive so as to serve as an electrode in a circuit of the implantable medical device 102. One or more leads 110, 112 are electrically coupled to the implantable electronic device 106 and extend via a vein 114 of the patient 104 to a tissue, e.g., a portion of a ventricle 116, a portion of an atrium 118, a nerve (not shown), a nerve bundle (not shown), or the like. The implantable medical device 102 may be programmed by using a programming unit 120, which may send instructions to and receive information from the implantable medical device 102 via radio-frequency signals.

Figure 2:
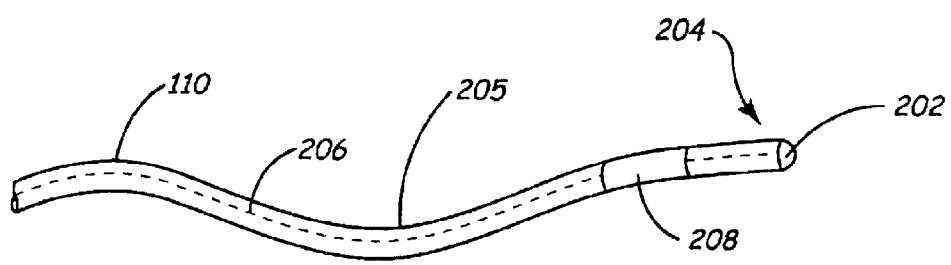
FIG. 2 is a stylized perspective view of an implantable medical device lead incorporating a shunting assembly according to a first or second embodiment of the present invention.

As shown in FIG. 2, one or more exposed, electrically-conductive electrodes, such as a tip electrode 202 or the like, are disposed generally near a distal end portion 204 of a body 205 of the lead 110, as well as a distal end of the lead 112 (not shown), if present. As indicated above, the tip electrode 202 may be used to sense electrical signals in a tissue, such as in the ventricle 116, in the atrium 118, in a nerve (not shown), in a nerve bundle (not shown), or the like. Further, the tip electrode 202 may be used to deliver electrical stimuli to the tissue, such as to deliver electrical stimuli to a portion, or portions, of a heart, to a nerve, or to a portion, or portions, of a nerve bundle. The lead 110 further includes a conductor set 206, electrically coupling the implantable electronic device 106, or an electrical extension (not shown) extending from the implantable electronic device 106, and one or more electrodes (e.g., the tip electrode 202 or the like) of the lead 110. Thus, the conductor set 206 extends from a proximal end portion (i.e., a portion joinable with the implantable electronic device 106 or the like) to the distal end portion 204 of the body 205.

Figure 3:
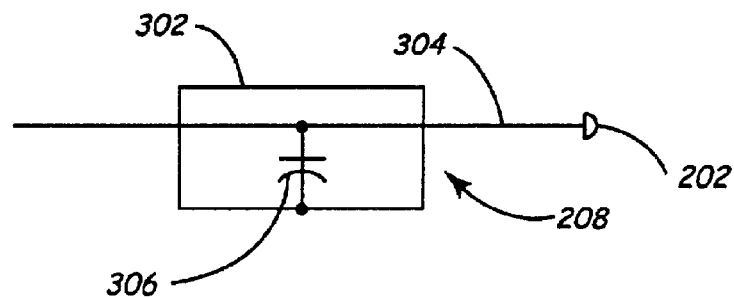
FIG. 3 is a schematic diagram of the first embodiment of the shunting assembly according to the present invention.

In a first embodiment, the implantable medical device 102 is a unipolar device in which the tip electrode 202 may serve as a cathode and the canister 108 may serve as an anode for pacing, stimulation, or sensing circuitry (not shown) of the implantable medical device 102. In this embodiment, as illustrated in FIGS. 2 and 3, a shunting assembly 208 includes a ring electrode 302, which is the portion of the shunting assembly 208 visible in FIG. 2. The conductor set 206 includes a tip conductor 304 that extends through the shunting assembly 208 to the tip electrode 202. The tip conductor 304 may be a continuous conductor or may be a plurality of conductors that are electrically interconnected. A capacitor 306 is electrically coupled between the tip conductor 304 and the ring electrode 302. The capacitor 306 may take the form of a single capacitive device, a plurality of capacitive devices that are electrically interconnected, or one or more capacitive devices electrically interconnected with other electronic devices.

Figure 4:
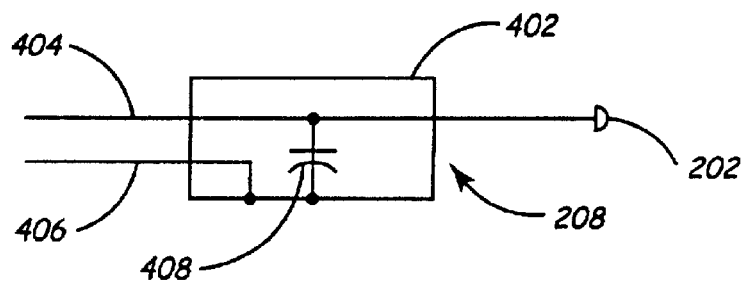
FIG. 4 is a schematic diagram of the second embodiment of the shunting assembly according to the present invention.

In a second embodiment, as illustrated in FIGS. 2 and 4, the implantable medical device 102 is a bipolar device in which the tip electrode 202 may serve as a cathode for the pacing, stimulation, or sensing circuitry (not shown) of the implantable medical device 102. In this embodiment, the shunting assembly 208 includes a ring electrode 402, which is the portion of the shunting assembly 208 visible in FIG. 2. Further, the ring electrode 402 may serve as an anode for the pacing, stimulation, or sensing circuitry of the implantable medical device 102. The conductor set 206 includes a tip conductor 404 that extends through the shunting assembly 208 to the tip electrode 202. The tip conductor 404 may be a continuous conductor or may be a plurality of conductors that are electrically interconnected. The conductor set 206 further includes a ring conductor 406 extending into the shunting assembly 208 and to the ring electrode 402. As in the tip conductor 404, the ring conductor 406 may be a continuous conductor or may be a plurality of conductors that are electrically interconnected. A capacitor 408 is electrically coupled between the tip conductor 404 and the ring electrode 302. The capacitor 408 may take the form of a single capacitive device, a plurality of capacitive devices that are electrically interconnected, or one or more capacitive devices electrically interconnected with one or more other electronic devices.

Figure 5:
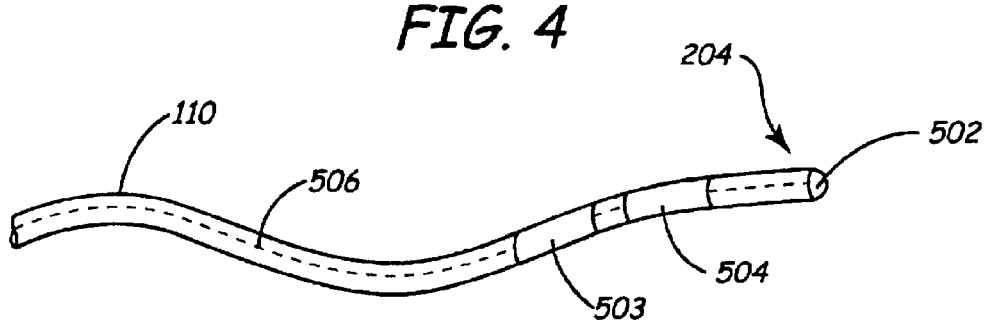
FIG. 5 is a stylized perspective view of an implantable medical device lead incorporating a shunting assembly according to a third embodiment of the present invention.
Figure 6:
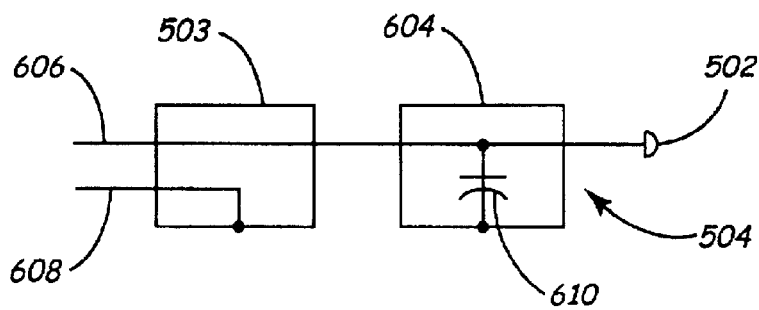
FIG. 6 is a schematic diagram of the third embodiment of the shunting assembly according to the present invention.

In a third embodiment, as illustrated in FIGS. 5 and 6, an implantable medical device 102 is a bipolar device in which the tip electrode 502 may serve as a cathode and a first ring electrode 503 may serve as an anode for the pacing, stimulation, or sensing circuitry (not shown) of the implantable medical device 102. In this embodiment, a shunting assembly 504 includes a second ring electrode 604, which is the portion of the shunting assembly 504 visible in FIG. 5. A conductor set 506 includes a tip conductor 606 that extends through the first ring electrode 503 and the second ring electrode 604 to the tip electrode 502. The tip conductor 606 may be a continuous conductor or may be a plurality of conductors that are electrically interconnected. The conductor set 506 further includes a ring conductor 608 extending to the first ring conductor 503. As in the tip conductor 606, the ring conductor 608 may be a continuous conductor or may be a plurality of conductors that are electrically interconnected. A capacitor 610 is electrically coupled between the tip conductor 606 and the second ring electrode 604. The capacitor 610 may take the form of a single capacitive device, a plurality of capacitive devices that are electrically interconnected, or one or more capacitive devices electrically interconnected with other electronic devices.

It is often advantageous for patents suffering from certain conditions to be examined using MRI processes or to be therapeutically treated using diathermy processes. However, patients having implantable medical devices within their bodies have typically been discouraged from undergoing such processes, as described above. The present invention, as illustrated in FIGS. 2–6, seeks to reduce this detrimental effect by dissipating induced current in the tip conductor 304, 404, 606 into tissue adjacent the ring electrode 302, 402, 604, as well as into tissue adjacent the tip electrode 202, 502. In this way, the heat, produced by the dissipating currents, is dispersed over a larger portion of tissue, thus decreasing the likelihood of damage to the tissue.

It is desirable, however, for pacing, stimulation, or sensed signals (e.g., signals of an electrogram or the like) being transmitted over the tip conductor 304, 404, 606, from or to the tip electrode 202, 502, not to be transmitted through the ring electrode 302, 402, 604. Rather, it is desirable for substantially all of such signals to be transmitted between the implantable electronic device 106 and the tip electrode 202, 502. Accordingly, the capacitors 306, 408, 610 perform filtering functions. A high frequency current such as is induced within the lead conductors during MRI or diathermy procedures are routed both to the ring electrodes 302, 402, 604, respectively, and the tip electrodes 202, 502. However, substantially all of the low-frequency pacing, stimulation, and/or sensed signals traveling over the tip conductors 304, 404, 606 are routed only to the tip electrodes 202, 502. For the purposes of this disclosure, the phrase "substantially all" of the pacing, stimulation, or sensed signals is defined as a level of signal at which the implantable medical device 102 is capable of operating properly.

The shunting assembly 208, 504 operates by employing the variable impedance characteristics of the capacitor 306, 408, 610. Generally, currents induced in conductors (e.g., the tip conductor 304, 404, 606) by energy fields emitted by MRI and diathermy equipment are greater than about one megahertz (MHz). Further, signals, such as pacing signals, stimulation signals, sensed signals, and the like, generally have frequencies of less than about 500 hertz (Hz). According to embodiments of the present invention, by taking into account the inherent electrical impedance of tissue of about 500 ohms (Ω), the capacitance of the capacitor 306, 408, 610 can be determined such that a portion of the current induced in the tip conductor 304, 404, 606 by the MRI or diathermy equipment is passed through the capacitor 306, 408, 610 to the ring electrode 302, 402, 604, while signals, such as pacing signals, stimulation signals, sensing signals, and the like are not passed through the capacitor 306, 408, 610, but are rather transmitted over the tip conductor 304, 404, 606 directly to the tip electrode 202, 502. In other words, the capacitor 306, 408, 610 acts as a filter to only allow currents having frequencies within a certain range to be routed to the ring electrode 302, 402, 604. In one embodiment, the capacitor 306, 408, 610, in combination with the impedance of the tip electrode 202 and the tissue, allows a high-pass filter to be created at certain frequencies such as those exceeding 1 MHz.

For example, given MRI-induced currents having a frequency of two MHz and a sensed signal (e.g., an electrogram signal, or the like) of 100 Hz, a one nanofarad (nF) capacitor (e.g., the capacitor 306, 408, 610, or the like) has a electrical impedance of about 80 Ω at a frequency of about two MHz and has a electrical impedance of about 1.6 megohms (MΩ) at a frequency of about 100 Hz, as demonstrated by the equation:

$$X_C = \frac{1}{2\pi fc}$$

wherein:

$X_C$=the impedance of the capacitor (Ω);

f=the frequency (Hz); and c=the capacitance of the capacitor (F).

Thus, in this example, the induced currents would pass through the tip electrode 202, 502, as well as through the capacitor 306, 408, 610 to the ring electrode 302, 402, 604, since the electrical impedance of the capacitor 306, 408, 610 is about 160Ω, which is less than the electrical impedance of tissue adjacent the tip electrode 202, 502 and the ring electrode 302, 402, 604 (500 Ω). In this case, the induced currents would be divided approximately 14 percent (80 Ω/580 Ω) to the tip electrode 202, 502 and approximately 86 percent (500 Ω/580 Ω) to the ring electrode 302, 402, 604. The sensed signal would be substantially unaffected, since the electrical impedance of the capacitor 306, 408, 610 is about 1.6 MΩ at 100 Hz, thereby providing a high-pass filtering effect.

In one embodiment, the electrical impedance of the capacitor 306, 408, 610 at frequencies typical of the induced current is below about one-fifth (about 20 percent) of the impedance of the tissue adjacent the tip electrode 202, 502 and adjacent the ring electrode 302, 402, 604 (e.g., 100 Ω in the example). In another embodiment, the electrical impedance of the capacitor 306, 408, 610 at frequencies typical of pacing, stimulation, or sensed signals is about ten times the impedance of the tissue adjacent the tip electrode 202, 502 and adjacent the ring electrode 302, 402, 604 (e.g., 5000 Ω in the example). Further, by sizing the surface area of the ring electrode 302, 402, 604 to be at least about three times the surface area of the tip electrode 202, 502, the current density may be reduced by at least about four times, thus leading to a commensurate reduction in temperature rise in the tissue adjacent the tip electrode 202, 502 and the ring electrode 302, 402, 604. In one embodiment, the surface area of the tip electrode 202, 502, as discussed herein, refers to the surface area of the tip electrode 202, 502 omitting any surface area attributed to microstructural pits, crevices, indentations, or the like that may be conventionally used to increase the electrical contact area of the tip electrode 202, 502. Such microstructural pits, crevices, indentations, or the like, in one embodiment, may have diameters of less than about 200 micrometers.

Figure 7:
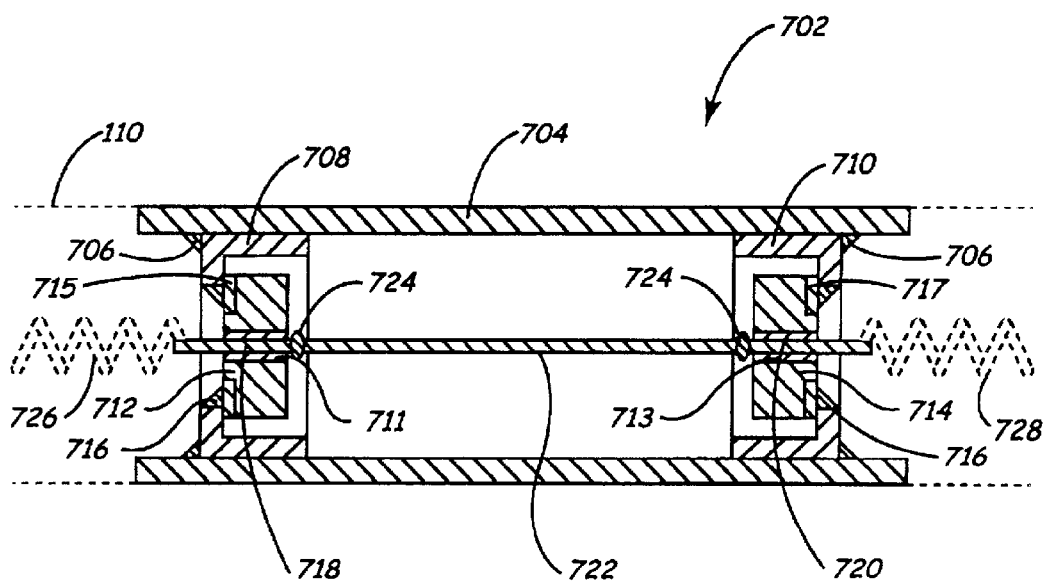
FIG. 7 is a partial cross-sectional view of an embodiment of the shunting assembly according to the present invention.

A shunting assembly 702 according to one embodiment of the present invention is illustrated in FIG. 7. The shunting assembly 702, which may, in one embodiment, be hermetically sealed, includes a tube 704 that is joined (e.g., by welds 706 or the like) to end caps 708, 710. Capacitors 712, 714 are electrically connected with and joined (e.g., by welds 716 or the like) to the end caps 708, 710, respectively. In one embodiment, the capacitors 712, 714 are discoidal capacitors or the like having central contacts 711, 713, respectively, and peripheral contacts 715, 717, respectively. The shunting assembly 702 further includes pins 718, 720 that are interconnected by a central conductor 722 by joints 724. The pins 718, 720 are electrically connected with the central contacts 711, 713, respectively. Further, the pin 718 is electrically connected with a proximal conductor 726 (shown in phantom) of the lead 110, which is electrically connectable with the implantable electronic device 106. The pin 720 is electrically connected with a distal conductor 728 (shown in phantom) of the lead 110, which is electrically connected with the tip electrode 202, 502 (FIGS. 2 and 5). Thus, the proximal conductor 726, the pin 718, the central conductor 722, the pin 720, and the distal conductor 728 comprise the tip conductor 304, 404, 606 (FIGS. 3, 4, and 6).

The capacitors 712, 714 are selected as described above, such that signals having a certain range or ranges of frequencies (i.e., induced currents) may flow both through the tip conductor 304, 404, 606 to the tip electrode 202, 502 and through the tube 704, which serves as the ring electrode 302, 402, 604. Signals having another range or ranges of frequencies (i.e., pacing, stimulation, sensed signals, or the like) may substantially only flow through the tip conductor 304, 404, 606 to the tip electrode 202, 502, as the capacitors 712, 714 have sufficient impedance to prevent the signals from flowing therethrough. While two capacitors 712, 714 are illustrated in FIG. 7, the present invention encompasses a shunting assembly 702 having one or more capacitors such as the capacitors 712, 714. Thus, the shunting assembly 702 is one embodiment of the shunting assembly 208, 504 illustrated in FIGS. 2–6.

Figure 8:
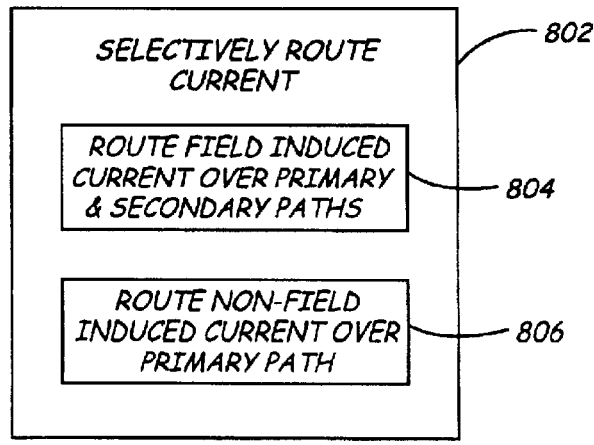
FIG. 8 is a block diagram of a method according to the present invention.

A method according to one embodiment of the present invention is illustrated in FIG. 8. In one embodiment, the method includes selectively routing an electrical current traveling through a conductor (e.g., the tip conductor 304, 404, 606 or the like) electrically coupled with body tissue (e.g., tissue of the patient 104 or the like) over at least one of a primary path and a secondary path to the body tissue based upon the characteristic of the electrical current (block 802). In one embodiment, the primary path may be through the tip conductor 304, 404, 606 and the tip electrode 202, 502. Further, the secondary path may be through the capacitor 306, 408, 610 and the ring electrode 302, 402, 604. In one embodiment, the characteristic of the electrical current comprises the frequency of the electrical current.

In another embodiment of the present invention, selectively routing the electrical current, as described above, further comprises routing the current over the primary path and the secondary path to the body tissue if the current is induced in the conductor by a field (block 804). In a further embodiment, selectively routing the electrical current, as described above, further comprises routing the current only over the primary path to the body tissue if the current is not induced in the conductor by a field (block 806).

Figure 9:
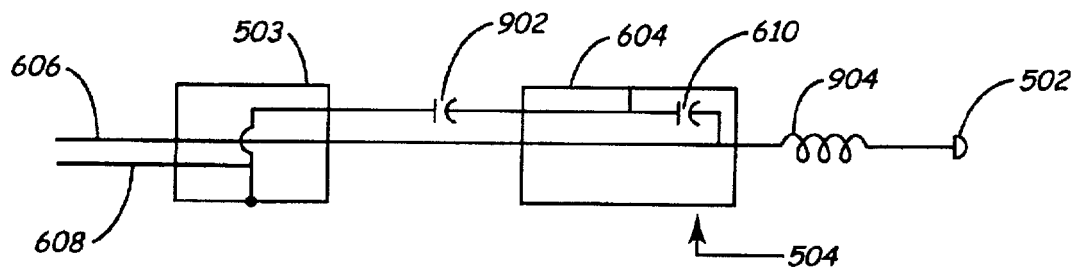
FIG. 9 illustrates yet another embodiment of the lead of FIG. 6.

FIG. 9 illustrates yet another embodiment of the lead of FIG. 6. As in FIG. 6, implantable medical device 102 is a bipolar device in which the tip electrode 502 may serve as a cathode and a first ring electrode 503 may serve as an anode for the pacing, stimulation, or sensing cardiac signals. Tip conductor 606 extends to tip electrode 502, and ring conductor 608 extending to first ring conductor 503. A capacitor 610 is electrically coupled between the tip conductor 606 and second ring electrode 604. The capacitor 610 may take the form of a single capacitive device, a plurality of capacitive devices that are electrically interconnected, or one or more capacitive devices electrically interconnected with other electronic devices. In this embodiment, second ring electrode 604 is further coupled via a second capacitor 902 to first ring electrode 503.

Also shown in FIG. 9 is an optional inductor 904. This inductor provides a high impedance path to the tip electrode 502 when high frequency signals are induced within conductor 606, as when the lead is subjected to RF electromagnetic fields. This high-impendence path further decreases the current flowing through the tip, thereby further minimizing heating effects at the lead tip. A similar inductor may be incorporated into any of the foregoing embodiments in a similar manner to that shown in FIG. 9. This inductor may be positioned at any location along conductor 606, but is optimally positioned substantially proximate to the tip electrode. In yet another embodiment, the inductor may be positioned at a more proximal location on conductor 606.

The embodiments discussed above include a shunting assembly. It may be noted, that in another embodiment of the invention, this shunting assembly is omitted, with only an inductor being used to limit current flow within one or more conductors of the lead.

Figure 10:
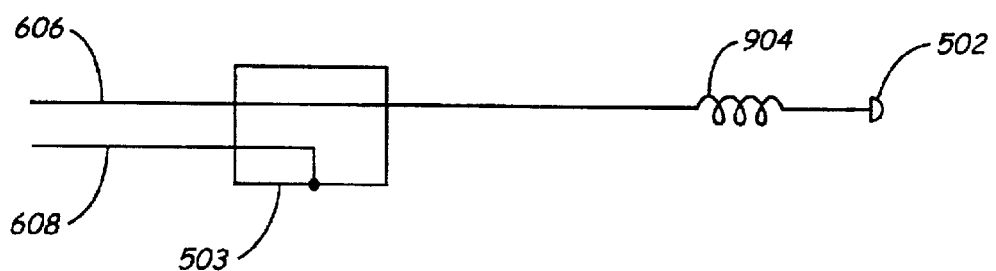
FIG. 10 illustrates an alternative embodiment of the lead of FIG. 6 that omits the shunting assembly.

FIG. 10 is a side view of a unipolar lead without a shunting assembly. Second ring electrode 604 is omitted, as is ring electrode 503. Inductor 904 is provided is relatively close proximity to tip electrode 502. As noted above, this inductor attenuates the frequencies of electrode magnetic signals used for MRI.

The foregoing examples discuss the use of passive components within the lead to minimize tissue injury when the lead is subjected to magnetic fields. In another embodiment, active components may be used instead of, or in addition to, passive components to reduce current flow within the lead. For example, a CMOS Field Effect Transistor (FET) may be used as a switch within a lead body to prevent current flow when the lead is exposed to RF electromagnetic energy.

Figure 11:
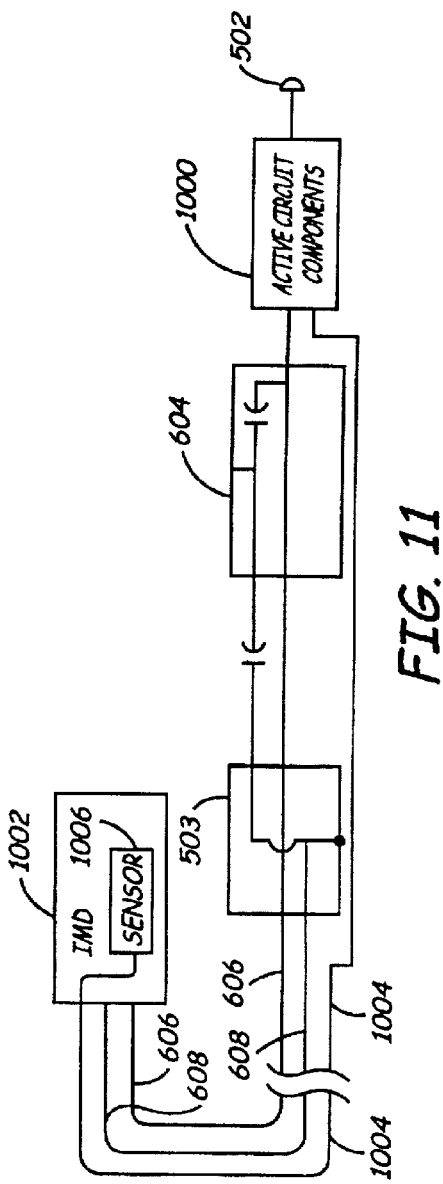
FIG. 11 illustrates still another embodiment of the lead of FIG. 6 that employs active circuit components to limit current flow within the lead.

FIG. 11 illustrates still another embodiment of the lead of FIG. 6. In this embodiment, one or more active circuit components 1000 are provided in series with conductor 606. Conductors 606 and 608 are shown coupled to an implantable medical device (IMD) 1002. A control signal 1004 is provided to one or more active components 1000 when the presence of a high-frequency electromagnetic field is detected. This detection may be accomplished using a frequency-sensitive hall-effective sensor, a magnetoresistive magnetic field sensor, or any other type of sensor 1006 that has been adapted to sense the presence of electromagnetic signals within a predetermined frequency range. In the illustrated embodiment, the sensor 1006 resides within the housing of the IMD, and the detection signal is provided by sensor and associated control circuitry as control signal 1004. In another embodiment, the sensor may be included within, or on, the lead body in proximity to the one or more active circuit components 1000, with the control signal being routed between the one or more active components 1000 and the sensor 1006.

As stated above, the one or more circuit components may include a FET, with the gate of the transistor being coupled to the control signal 1004 so that the flow of current through the distal portion of conductor 606 may be selectively disabled. This prevents all current from flowing through the tip electrode 502 when the lead is placed within a high-frequency electromagnetic field. Any other active circuit component that may be adapted for use in a switching network and employable to control currents induced by RF electromagnetic fields as discussed herein may be used in the alternative. It may be noted that in another embodiment, the lead of FIG. 10 need not include ring electrodes 503 and 604. In this instance, tissue heating and subsequent injury at tip electrode 502 is prevented by opening the switching circuit comprised of active circuit components 1000. Finally, it may be noted that active circuit components may be incorporated into any of the foregoing lead embodiments in a similar manner as shown in FIG. 10.

Figure 12:
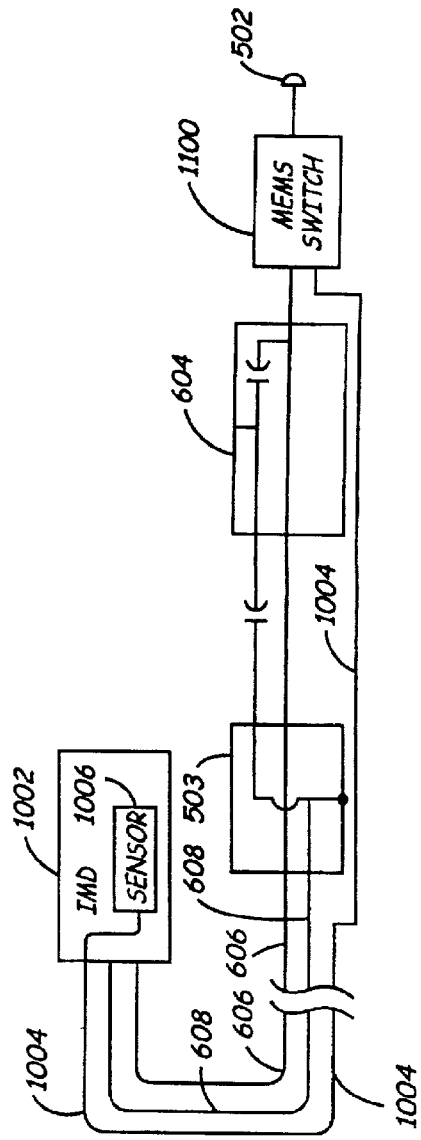
FIG. 12 illustrates another embodiment of the lead of FIG. 6 that employs Micro-Electrical-Mechanical system (MEMs) switches within the lead.

In yet another embodiment of the invention, Micro-Electrical-Mechanical system (MEMs) switches may be used in place of one or more transistor networks in a manner similar to that discussed above. For example, FIG. 12 illustrates MEMs switching network 1100 coupled to control signal 1004 to control current flow in conductor 606. Such switches, which have dimensions in a range of less than 10 microns, can be manufactured on silicon, as described in U.S. Pat. Nos. 6,070,101, 6,081,748, 6,122,545, and 6,148,234 incorporated herein by reference in their entireties. These switches may be opened or closed using control signals such as control signal 1004. Use of MEMs technology within an implantable medical device is described in commonly-assigned U.S. Patent Application entitled "MEMs Switching Circuit for an Implantable Medical Device", incorporated herein by reference in its entirety. As discussed above in reference to FIG. 10, the lead of FIG. 11 need not include ring electrodes 503 and 604. Tissue heating is prevented by opening the MEMs switching network 1100. MEMs components may be incorporated into any of the foregoing lead embodiments in a similar manner as shown in FIG. 11.

While the operation of the present invention has been disclosed relative to energy fields emitted by MRI and diathermy equipment, the present invention is not so limited. Rather, the operation of the present invention is equally applied to energy fields emitted by equipment other than MRI and diathermy equipment.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. An electrical lead, comprising:
   an elongate body having a proximal end portion and a distal end portion;
   a first electrode disposed near the distal end portion of the elongate body;
   a first conductor electrically coupled to the first electrode;
   a second electrode disposed adjacent the elongate body;
   a capacitive device electrically coupled to the first conductor and the second electrode; and
   a component coupled to the first conductor to selectively limit current through the first electrode.

2. The lead of claim 1, wherein the component is an inductor.

3. The lead of claim 1, wherein the component is a switch.

4. The lead of claim 3, wherein the component is coupled to a sensor capable of detecting an electromagnetic field.

5. The lead of claim 4, wherein the sensor is capable of detecting an electromagnetic field in a predetermined frequency range.

6. The lead of claim 5, wherein the switch includes active circuit components.

7. The lead of claim 5, wherein the switch includes Field Effect Transistors (FETs).

8. The lead of claim 5, wherein the switch includes at least one Micro-Electrical-Mechanical System (MEMs) switch.

9. The lead according to claim 1, further comprising a second conductor extending between the proximal end portion of the elongate body and the second electrode end being electrically coupled to the second electrode.

10. The lead according to claim 1, further comprising:
    a third electrode disposed adjacent the second electrode and joined to the elongate body; and
    a second conductor extending between the proximal end portion of the elongate body and the third electrode and being electrically coupled to the third electrode.

11. The lead according to claim 1, wherein the capacitive device further comprises a discoidal capacitor having a central contact and a peripheral contact;
    the first conductor is electrically coupled with the central contact; and
    the second electrode is electrically coupled with the peripheral contact.

12. The lead according to claim 1, wherein:
    the first electrode and the second electrode are capable of being electrically coupled with body tissue;
    the first conductor is capable of transmitting an electrical current; and
    the capacitive device has an electrical impedance substantially less than electrical impedance of the body tissue at signal frequencies greater than those used to sense biological signals or deliver electrical stimulation to the body tissue.

13. The lead according to claim 1, wherein:
    the first electrode and the second electrode are capable of being electrically coupled with body tissue;
    the first conductor is capable of transmitting an electrical current; and the capacitive device has an electrical impedance substantially greater than an electrical impedance of the body tissue at signal frequencies used to sense biological signals or deliver electrical stimulation to the body tissue.

14. The lead according to claim 1, wherein an area of the second electrode is at least three times an area of the first electrode.

15. The lead according to claim 1, wherein the capacitive device is capable of allowing at least a portion of a current, induced in the first conductor by a field, to be routed to the second electrode.

16. A medical electrical lead for an implantable medical device having a sensor to sense a predetermined physiological condition, comprising:
   an elongate body;
   an electrode;
   a component coupled to the elongate body to limit the flow of current through the electrode upon detection of the predetermined physiological condition.

17. The lead of claim 16, wherein the sensor is adapted to sense an electromagnetic field.

18. The lead of claim 17, wherein the component is configured to limit the flow of current through the electrode upon detection of an electromagnetic field in a predetermined frequency range.

19. The lead according to claim 18, wherein the component is an active circuit component.

20. The lead according to claim 19, wherein the component is a field effect transistor.

21. The lead according to claim 18, wherein the component is a Micro Electrical-Mechanical system (MEMs) switch.

22. The lead according to claim 18, and further comprising a shunting assembly coupled to the elongate body to dissipate heat when the lead is exposed to the electromagnetic field in the predetermined frequency range.

23. The lead according to claim 22, wherein the shunting assembly comprises a capacitive device.

24. The lead according to claim 23, wherein the capacitive device is a discoidal capacitor having a central contact and a peripheral contact, wherein the electrode is electrically coupled with the peripheral contact, and further comprising a conductor electrically coupled with the central contact.

25. A method of utilizing a medical electrical lead, wherein the lead includes an elongate body and an electrode coupled to the elongate body, comprising the steps of:
   a.) providing a primary current path within the elongate body to the electrode;
   b.) limiting current in the primary current path when a predetermined condition is present within the medical electrical lead;
   c.) providing at least one secondary current path to carry current when the predetermined condition is sensed.

26. The method of claim 25, wherein the predetermined condition of step b.) is the presence in the primary current path of a current having a frequency within a predetermined frequency range.

27. The method of claim 26, wherein step b.) includes limiting current via a inductor placed within the primary current path.

28. The method of claim 25, wherein step b.) comprises sensing an electromagnetic field, and limiting current when the sensed electromagnetic field has a magnetic field strength within a predetermined range.

29. The method of claim 28, wherein step b.) comprises limiting current by opening a switch.

30. The method of claim 29, wherein step b.) comprises opening a MEMs switch.

31. The method of claim 28, wherein step b.) comprises using an active circuit component to limit current flow.

32. The method of claim 31, wherein step b.) comprises using an FET to limit current flow.

33. The method of claim 25, and further including:
   d.) routing current from the primary current path to the secondary current path when the predetermined condition is present.

34. The method of claim 33, wherein step d.) includes providing a capacitor between the primary current path and the secondary current path to shunt current having a frequency within a predetermined frequency range there between.

* * * * *